United States Patent [19]

Bellhouse

[11] 4,075,091
[45] Feb. 21, 1978

[54] METHOD FOR EFFECTING HEAT OR MASS TRANSFER

[75] Inventor: Brian John Bellhouse, Wendlebury, near Bicester, England

[73] Assignee: National Research Development Corporation, London, England

[21] Appl. No.: 572,826

[22] Filed: Apr. 29, 1975

Related U.S. Application Data

[63] Continuation of Ser. No. 371,986, June 21, 1973, abandoned.

[30] Foreign Application Priority Data

June 28, 1972 United Kingdom .............. 30288/72
Mar. 29, 1973 United Kingdom .............. 15117/73

[51] Int. Cl.$^2$ ..................... B01D 13/00; A61M 1/03
[52] U.S. Cl. ................... 210/19; 210/22 A; 210/321 B; 195/1.8
[58] Field of Search ............. 210/19, 22, 321, 500 M; 23/258.5 M, 258.5 MH; 195/1.8

[56] References Cited

U.S. PATENT DOCUMENTS

| | | | |
|---|---|---|---|
| 3,060,934 | 10/1962 | Claff et al. | 210/321 X |
| 3,342,729 | 9/1967 | Strand | 210/500 M X |
| 3,631,986 | 1/1972 | Sausse | 210/321 |
| 3,648,754 | 3/1972 | Sephton | 210/321 X |
| 3,704,223 | 11/1972 | Dietzsch et al. | 210/22 X |
| 3,864,248 | 2/1975 | Granger et al. | 210/321 X |

Primary Examiner—Frank A. Spear, Jr.
Attorney, Agent, or Firm—Cushman, Darby & Cushman

[57] ABSTRACT

A method and apparatus for effecting heat or mass transfer between two fluids through a membrane comprises a conduit for flow of one fluid, said conduit being at least partly defined by said membrane and the configuration of said conduit in a plane orthogonal to the general direction of flow varying periodically along the general direction of flow either inherently or in response to fluid pressure therein in such a manner that when said fluid is pulsated along the line of the general direction of flow a component of motion is induced therein which is mutually orthogonal to the surface of the membrane and general direction of flow. In preferred embodiments the conduit configuration varies periodically along the general direction of flow in order to give rise to separation and reattachment of flow at a multiplicity of zones within the conduit, whereby secondary flow is induced within said zones. The apparatus is particularly applicable to blood oxygenation and dialysis.

6 Claims, 6 Drawing Figures

METHOD FOR EFFECTING HEAT OR MASS TRANSFER

This is a continuation, of application Ser. No. 371,986 filed June 21, 1973 now abandoned.

This invention relates to a method for effecting heat or mass transfer across a membrane and has particular relevance to blood oxygenators and dialysers.

Since the development of the first membrane blood oxygenators and dialysers membranes have been made progessively thinner and more effective. The resistance set up by blood flowing in channels or tubes have however been found to severely limit the rate of mass transfer across the membrane.

A method and apparatus has now been devised by means of which excellent transfer rates to or from blood may be achieved.

According to the present invention, apparatus for effecting heat or mass transfer between two fluids through a membrane comprises a conduit for flow of one fluid, said conduit being at least partly defined by said membrane and the configuration of said conduit in a plane orthogonal to the general direction of flow varying periodically along the general direction of flow either inherently or in response to fluid pressure therein in such a manner that when said fluid is pulsated along the line of the general direction of flow, a component of motion is induced therein which is mutually orthogonal to the surface of the membrane and direction of flow.

In preferred embodiments according to the present invention, the conduit configuration varies periodically along the general direction of flow (either inherently or in response to fluid pressure therein) in order to give rise to separation and reattachment of the flow at a multiplicity of zones within the conduit whereby secondary flow is induced within said zones. The zones which can vary considerably in configuration are generally spaced one from another by constrictions to flow through the conduit. When fluid is pulsated across a constriction, the flow is detached therefrom and reattaches at a neighbouring constriction with eddy formation in the zone between the constrictions. The eddies which reduce the boundary layer effect generally take the form of vortices, the axes of which are transverse to the general direction of flow. It is believed that the vortices are formed primarily during deceleration of fluid which has been subjected to pulsation, the vortices tending to be ejected during acceleration. It will be appreciated that when the fluid in the conduit is blood, flow must be non-turbulent if trauma is to be avoided. The present invention provides means by which an effective mixing flow can be induced in blood substantially without turbulence.

The conduit surface, typically the surface of the membrane, may vary along the general direction of flow to provide the zones either intermittently or preferably continuously as with an undulating membrane surface. The zones may take a variety of configurations. In particular, they may extend across the surface of the conduit transverse to the direction of flow to provide furrows or may be present as local depressions such as dimples in a conduit surface, such depressions preferably having curved bases and conveniently being hemispherical.

When the surface of the membrane is shaped into zones in response to the pressure of fluid in the conduit, one or more means are provided associated with the membrane for constraining the latter to adopt the required configuration in response to the pressure of fluid therein. Where the membrane is extremely thin as is generally the case when blood is to be oxygenated or dialysed, the means for constraining the membrane may also act as a membrane support. If so desired however, zones may be provided in the region of the membrane surface by a shaped member within the conduit and conveniently formed prior to insertion therein.

Although the transfer membrane can be provided in a variety of configurations, laminar and tubular membranes are preferred. Laminar membranes are generally employed in pairs which together constitute a membrane envelope, and the requisite zones are preferably provided by furrowing of the membrane surface in a direction transverse to the general direction of flow, although other configurations for the zones may be adopted if so desired. Laminar membranes, when extremely thin, require support for example from a sheet or the like possessing corrugations which define the ridges and furrows in the membrane. It is generally preferable for ridges and furrows in the laminar membranes constituting a membrane envelope to be located opposite each other without significant displacement. The corrugated sheet which may be rigid and formed for example from a plastics material by extrusion, pressing or moulding is conveniently provided with substantially planar portions at, or in the region of, two or more edges thereof, the surface of which portions serve to space the ridges in the sheet from those of its neighbour. The latter portions are preferably integral with the sheet. A membrane envelope may be secured between the portions of two adjacent sheets by mechanical pressure applied thereto and preferably with the use of adhesive applied between the envelope and the portions. Adhesive is also preferably applied in the ridges of the sheet and the membranes. In such embodiments the membrane may be furrowed before commencement of fluid flow thereacross but preferably the membrane is planar or only slightly furrowed before introduction of pressurised fluid to the surface thereof which forces the membrane into corrugations in the sheet to form adequate furrows therein.

When tubular membranes are employed, which membranes are preferably circular in cross section, the zones are preferably provided by circumferential furrowing. Although the latter configuration for the zones is preferred, others may be employed if so desired. With tubular membranes it may be found particularly convenient to employ a shaped member in the conduit to provide convenient to employ a shaped member in the conduit to provide zones in the region of the membrane surface. The member may for example be a rod or tube possessing circumferential ridges along the length thereof. When in place within the conduit the zones between the ridges are located in the region of the membrane surface and are hence associated therewith.

It will be appreciated that values for the dimensions of the zones i.e. the depth, the length along the general direction of flow and, where applicable, for the spacing between constrictions separating the zones and located opposite each other in the conduit may be established by simple experiments. In general, however, the length of the zones i.e. where furrows are provided, the pitch thereof, should be greater than the depth and greater than the spacing. The zone length (L), period of oscillation of the fluid (for reciprocating pulsatile flow) (T) at peak velocity required by the fluid during a pulse (U) are usually related by the equation $L/TU < 10$ and preferably <1, for the formation of vortices during the pulse.

Although the foregoing description has generally been directed to apparatus comprising conduits provided with zones associated with membrane surface, the present invention also includes within its scope embodiments in which the provision of such zones is not essential. Particularly when the embodiments comprise a tubular conduit there is provided means located within the conduit for constraining fluid within said conduit to follow a substantially helical path therethrough. In such embodiments the membrane itself is conveniently tubular and the means for constraining the fluid flow in a helical path may be formed by twisting a strip of material about its longitudinal axis to provide an insert which preferably fits tightly inside the tube. When fluid in pulsated in the conduit, secondary rotary flow is induced in the fluid the axis of which lies generally in the direction of flow. Such secondary flow enhances the mixing action promoted by the helical fluid motion and facilitates transfer through the membrane.

The type of membrane to be used in apparatus according to the present invention will of course depend on the application. For neat exchange, the membrane is generally of metal, for oxygenation of blood or removal of carbon dioxide therefrom the membrane may be of silicone elastomer or a polyester such as Tyrann, and for haemodialysis or reverse osmosis, the membrane may be of cellophane, Cuprophane or Tyrann. It will be appreciated that all materials which contact the blood e.g. those from which the conduit and membrane are fabricated should be blood compatible.

When the present invention is used for dialysis, the second conduit for dialysing fluid is preferably provided with means for generating a secondary mixing flow therein. The secondary flow in this case may be turbulent or non-tubulent and the dialysing fluid may be pulsated or moved through the conduit under steady flow conditions. Preferably however, the dialysing fluid follows a helical path through the second conduit, by means for example of a strip of suitable material twisted about its longitudinal axis and inserted in the conduit. When the dialysing fluid is pulsated along the line of the general direction of flow, vortex formation is promoted therein.

Although in some applications of the present invention, fluid in the conduit may be pulsated unidirectionally, reciprocatory pulsatile flow is generally preferably. Particularly when blood is to be oxygenated or dialysed, the rate of oscillation typically lies between 50 to 180 cycles per minute.

By means of an appropriate pump and valve assembly communicating with the conduit, blood therein may be subjected to reciprocatory movement imposed on displacement through the conduit. Typically the backward movement of the fluid amounts to half or more of the forward movement.

Fluid may be transferred to the conduit inlet under gravitational pressure or otherwise (e.g. by a pump). When for example blood is to be oxygenated or dialysed, the latter method may be employed by placing the apparatus below (e.g. 50–100 cm below) the level of the patient to whom it is connected, the pressure of fluid, (gas or dialysing fluid) to the other side of the membrane being lower than the gravitational pressure. The fluid passes from the conduit outlet into a pump which on actuation returns part of the fluid to the conduit and part in the direction of flow for recirculation.

A non-return valve is usually located between the conduit outlet and the pump and/or downstream from the pump. When the valve is located between the outlet and the pump, return flow is possible because the valve comes into operation only after actuation of the pump has commenced. When pumping action ceases, the forward pulse again commences and reciprocatory pulsatile flow continues indefintely. The pump employed is preferably tubular and of the type generally described in U.K. Pat. No. 1268049 and the non-return valve is preferably of the tricuspid type generally described in U.K. Pat. No. 1315844 corresponding to U.K. application No. 22954/70.

It will be appreciated that more complex systems may be provided in accordance with the present invention. In one such system, a first non-return valve communicates with the conduit inlet through a first pump and the conduit outlet communicates with a second pump which is connected with a second non-return valve communicating with a third pump connected to the fluid output through a third non-return valve. The stroke rates of the pumps are preferably identical and the capacities of the pumps are such that when pumping action is correctly phased, fluid in the conduit is subjected to reciprocating movement imposed on displacement therethrough.

Embodiments of the present invention will now be described by way of example only with reference to the accompanying drawings of which:-

Figure 1:
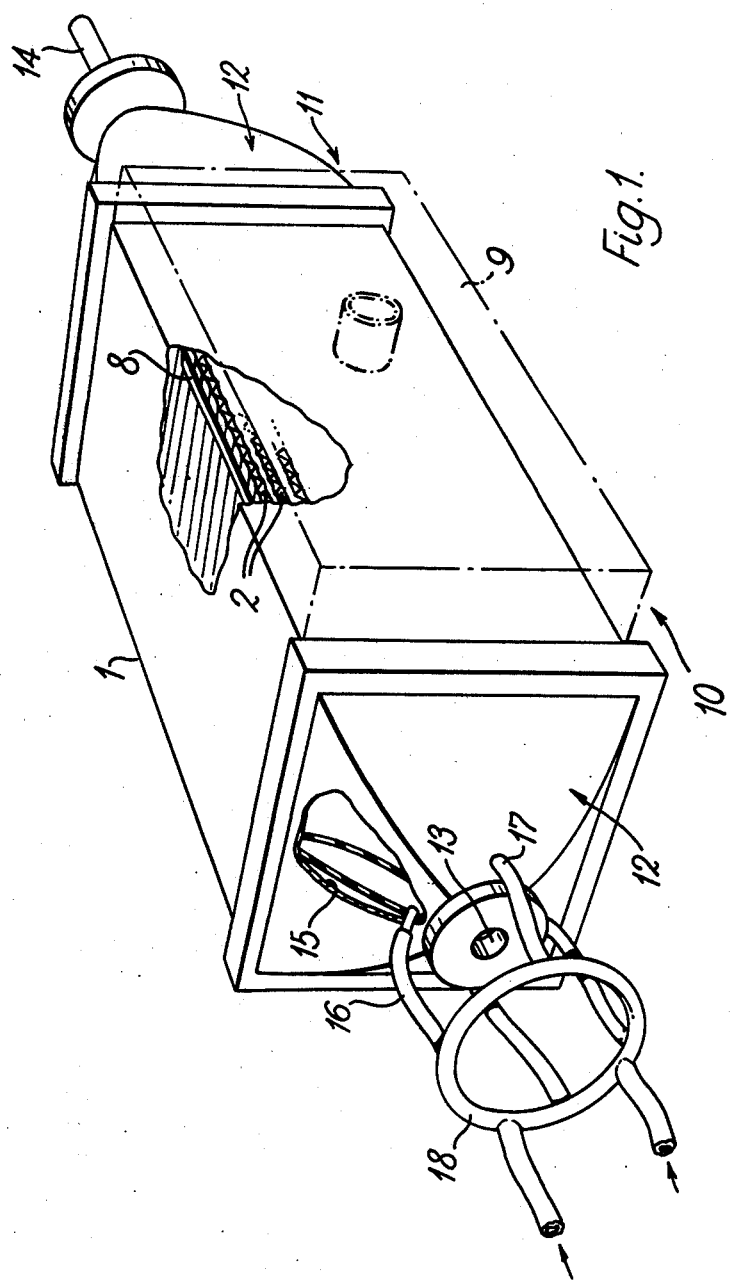
FIG. 1 shows a perspective view of apparatus suitable for the oxygenation of blood, in which apparatus part of the exterior surface has been moved to show the interior.
Figure 2:
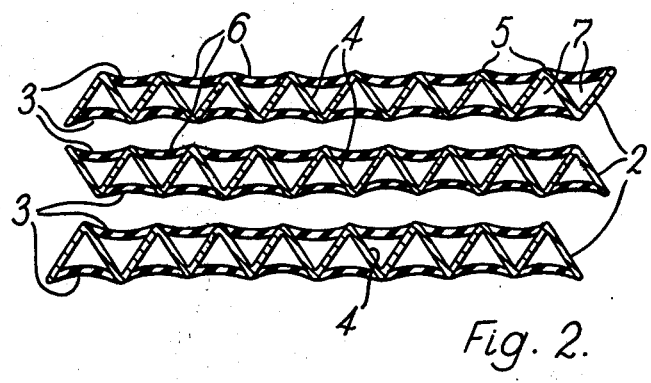
FIG. 2 shows a vertical section along the centre line of the centre portion of the apparatus depicted in FIG. 1.
Figure 3:
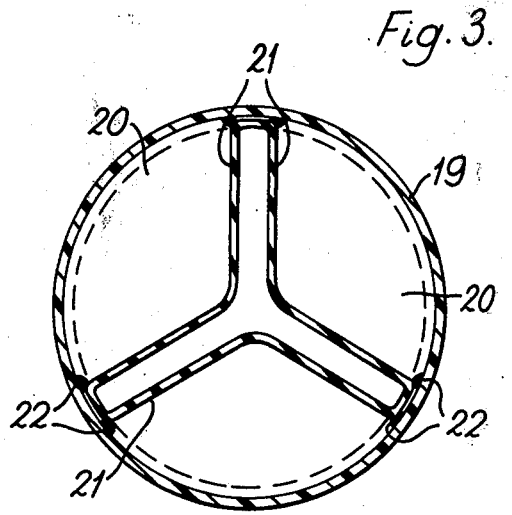
FIG. 3 shows a transverse cross-sectional view of a tubular pump suitable for use with the apparatus shown in FIG. 1.

Referring now to FIGS. 1 to 2, the apparatus comprises a stack 1 of plates 2 each of which consists of two membranes 3 separated by and supported on a corrugated stainless steel sheet 4. The plates 2 are made by applying a suitable silicone rubber adhesive to a stretched corrugated sheet 4 followed by laying a silicone elastomer membrane of thickness 0.00125 inches 3 over the ridges 5 in the sheet 4 which is then allowed to relax. Two membranes 3 may be applied to one sheet 4, one at each corrugated face, in one operation. On relaxation furrows 6 are formed in the membrane 3 the bottoms of which are spaced from the metal sheet 4 to allow oxygen flow in channels 7 along the outside of each furrow 6. The pitch of the furrows is 2 mm. and depth 0.5 mm. Each plate is vertically spaced from its neighbours by pairs of spacing strips of stainless steel 8 sealed to the membrane near opposing edges and parallel thereto, thereby forming a membrane envelope between adjacent plates for blood flow at right angles to the flow of oxygen. The disposition of adjacent plates 2 is such that the ridges 5 in the membrane 3 vertically correspond, the ridges being separated by 0.4 mm. Adjacent membranes are if desired sealed at their edges to provide further security against leakage of blood through any gap inadvertently present between the spacing strips 8 and membrane 3. The stack 1 is provided with an oxygen distribution chamber 9 which communicates with the channels 7 between the outside of the furrows and each sheet 4. The stack also communicates with a forward flow pump 10 and a return flow pump 11 located at opposite ends thereof and providing for reciprocatory pulsatile flow through the stack. Each of the pumps 10, 11 which are identical, comprises a generally pyramidal outer casing 12 the apex of which is formed into a blood inlet and outlet port 13, 14 communicating with the interior of the casing. Both pumps are provided with four inflatable sacs 15, (only one is shown), each of which has three edges which are disposed along the edges of the pyramidal casing. The sacs 15 are sealed along their edges to the corresponding edges of the casing. The sac interiors 16 communicate with air conduits 17 interconnected a short way from the pump by tubing 18 which is in turn connected to a system (not shown) adapted to rapidly alternate between supplying air under pressure and venting to atmosphere. The blood inlet and outlet ports 13, 14 are connected to non-return valves (not shown) of the tricuspid type, and the non-return valve at the output side communicates with a third pump shown in cross-sectional view in FIG. 3 which is generally tubular in form, which pump is connected to a third tricuspid return valve (not shown).

The tricuspid non-return valves are of the type generally described in U.K. Pat. No. 1315844 corresponding to U.K. application No. 22954/70. The suture ring is, however replaced by connecting flanges located at each end. The tubular pump is of the form generally described in U.K. Pat. No. 1,268,049 and comprises a generally tubular outer casing (inside which are disposed three sacs) each being bounded in part by a portion of the curved outer casing and in part by flexible sheets (anchored at opposing edges to the outer casing along the length thereof). The sacs are delatable by air entering through ports (not shown) located in the outer casing thereby to eject blood contained within the space between the sacs. On relaxation the flexible sheets adopt the configuration shown in the dotted line of FIG. 3. The pump is preferably provided with an inner removable lining to contain the blood and separate it from the sacs. The lining acts as a safeguard to minimise risk of air leakage from the sacs to the blood, and may easily be sterilised.

In other embodiments, preferred for the oxygenation of blood, all or any of the pumps are provided with sacs possessing two or more contiguous layers of material disposed between the driving gas and the pumped fluid.

The apparatus is operated by setting the controls so that the stroke of each of the three pumps is 80 beats per minute and so that they are correctly phased. The forward flow pump 10 is actuated while the return flow pump 11 and tubular pump 19 relax to receive blood from the stack and from the return pump respectively. The tubular pump then expels blood to the output and the forward flow pump synchronously relaxes to receive blood from the input via the non-return valve. The cycle is completed on contraction of the return flow pump to transfer blood from the stack to the forward flow pump. When the above phase relationships are established the capacity of each pump is adjusted so that blood is displaced through the stack by about 2 cm. at each beat. The capacity of the forward flow pump is conveniently 112 cc., that of the return pump 37 cc. and that of the tubular pump 75 cc.

In a smaller embodiment of the present invention, a single blood flow channel is bounded by a silicone elastomer membrane envelope of surface area 200 cm$^2$., the membrane being 0.0015 inches thick. The oxygen transfer rate at a blood flow rate 50 ml./min. is 130 ml. $O_2$/min./m$^2$, the maximum possible for the particular membrane.

In yet a further embodiment containing three blood flow channels, the membrane thickness is 0.00125 inches and total area 1450 cm$^2$. The oxygen transfer rate is 140 m$10_2$/min/m$^2$ at a mean blood flow rate 400 ml./min. and oscillation frequency 120/min. No blood trauma is caused by the oxygenator during closed circuit pumping undertaken for periods up to four hours.

Comparisons of the present system with those of other membrane oxygenators show increases in oxygen transfer rates by factors of five or six.

Figure 4:
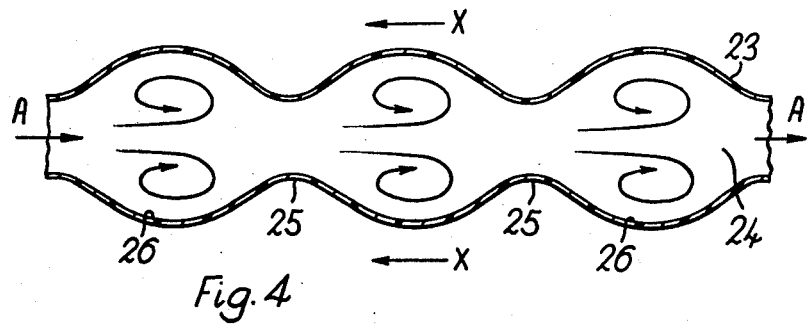
FIG. 4 shows a section along the length of part of a first tubular membrane suitable for use as a conduit according to the present invention.

Referring now to FIG. 4, a transfer membrane of circular cross-section 23 forms a conduit 24 for flow of fluid therethrough. The conduit has constrictions 25 along the length thereof which space zones in the form of circumferential furrows 26 one from another. When fluid in the conduit is pulsated along the length thereof, in the direction shown by the arrow A vortices are set up in the zones as shown. When the fluid is blood and dialysing fluid or a gas comprising oxygen is passed over the outer surface of the membrane dialysis or oxygenation can be effected.

Figure 5:
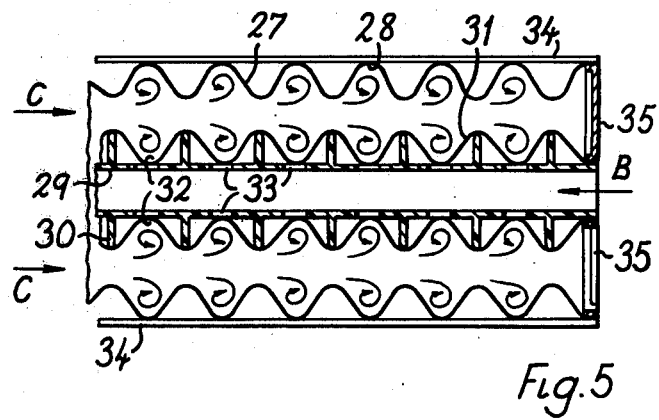
FIG. 5 shows a section along the length of part of a second tubular membrane incorporating an insert.

Referring now to FIG. 5, a tubular transfer membrane 27 provided with circumferential furrows 28 has disposed within it a tubular member 29 on which are mounted annular discs 30 which support an inner transfer membrane 31, also formed into circumferential furrows 32. The inner membrane 31 is located in place on the member 29 by means of adhesive applied between the disc and the membrane. The tubular member 29 is provided with apertures 33 which can conduit an oxygenating gas passed along the interior of the member in the direction shown by arrow B to the surface of the inner membrane 31. The outer membrane is supported by adhesion to an elongate membrane 34 and the inner membrane by support ring provided with struts 35. A second flow of oxygenating gas (not shown) can be provided to the outer surface of the membrane 27 and when blood is pulsated along the space between the membranes in the direction shown by arrow C, vortices are formed in the furrows as shown, which enhance the rate of transfer of oxygen from the latter gas and from the gas flow B into the blood.

Figure 6:
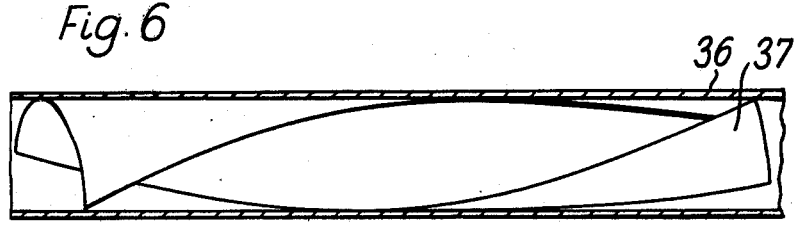
FIG. 6 shows a section along the length of part of a third tubular membrane incorporating an insert shown in perspective view.

Referring now to FIG. 6, a tubular transfer membrane 36 with a uniform interior surface has disposed within it a member formed by twisting a strip of blood compatible material about its axis and tightly fitting the interior membrane 37. The member provides a helical path for blood pulsated through the conduit which blood is oxygenated or dialysed by a flow of oxygenating gas or dialysing fluid to the outer surface of the membrane 36.

I claim:

1. A method for effecting heat or mass transfer between blood and a fluid through a transfer membrane, in which oneof said fluids is passed in pulsatile flow through a conduit at least partly defined by the membrane to give rise to substantially non-turbulent rotatory secondary fluid flow pattern in each of successive hollows in the membrane, the rotatory flow having components of motion parallel and components of motion perpendicular to the general direction of flow in the conduit.

2. A method according to claim 1, in which the fluid in said conduit is blood.

3. A method according to claim 2, in which the blood is subjected to reciprocatory pulsatile flow through the conduit.

4. A method according to claim 3, in which the rate of said flow is within the range 50–180 oscillations per minute.

5. A method according to claim 2 in which oxygen is transferred through the membrane to the blood in said conduit.

6. A method according to claim 3, in which blood impurities are removed through said membrane from blood within said conduit to a dialysing fluid without said conduit.

* * * * *